(12) United States Patent
Müller et al.

(10) Patent No.: US 6,770,299 B1
(45) Date of Patent: Aug. 3, 2004

(54) LIPID MATRIX-DRUG CONJUGATES PARTICLE FOR CONTROLLED RELEASE OF ACTIVE INGREDIENT

(75) Inventors: Rainer H. Müller, Berlin (DE); Carsten Olbrich, Berlin (DE)

(73) Assignee: PharmaSol GmbH, Berlin (DE)

( * ) Notice: Subject to any disclaimer, the term of this patent is extended or adjusted under 35 U.S.C. 154(b) by 0 days.

(21) Appl. No.: 09/959,706

(22) PCT Filed: May 8, 2000

(86) PCT No.: PCT/EP00/04111

§ 371 (c)(1),
(2), (4) Date: Jan. 14, 2002

(87) PCT Pub. No.: WO00/67800

PCT Pub. Date: Nov. 16, 2000

(30) Foreign Application Priority Data

May 7, 1999 (DE) .......................................... 199 20 908
Dec. 27, 1999 (DE) .......................................... 199 64 085

(51) Int. Cl.$^7$ .............................. A61K 9/14; A61K 9/16
(52) U.S. Cl. ........................ 424/489; 424/490; 424/491; 424/492; 424/493
(58) Field of Search ................................. 424/489, 490, 424/491, 492, 493

(56) References Cited

U.S. PATENT DOCUMENTS 5,554,728 A * 9/1996 Basava et al. .............. 530/327

6,288,040 B1 * 9/2001 Muller et al. ................. 514/21

FOREIGN PATENT DOCUMENTS

| WO | WO 95/32002 | * 11/1995 |
| WO | WO 96/14830 | * 5/1996 |
| WO | WO 96/22773 | * 8/1996 |

OTHER PUBLICATIONS

*Chemical Abstracts*, Aug. 15, 1994, p. 48, vol. 121, No. 7, abstract No. 073228g, Chen Z et al. "Tributyrin: A prodrug of butyric acid for potential clinical application in differentiation therapy."

Ahlin et al, "Optimization of procedure parameters and physical stability of solid lipid nanoparticles in dispersions", *Acta Pharm.*, 1998, vol. 48.

*Chemical Abstracts*, Jul. 11, 1994, p. 594, vol. 121, No. 2, abstract No. 17931u, Scriba, G., "Synthesis and in vitro evaluation of 4–(2–glyceryl)butyric acid: a glyceride mimic for drug delivery via drug–lipid conjugates."

* cited by examiner

*Primary Examiner*—Thurman K. Page
*Assistant Examiner*—S. Tran
(74) *Attorney, Agent, or Firm*—Jeffrey S. Melcher; Manelli Denison & Selter, PLLC

(57) ABSTRACT

The invention relates to particulate active ingredient vehicles which are in the solid aggregate state at room temperature (20° C.) and consist of a pure lipid-drug conjugate (LDC) or a mixture of several LDCs as particle matrix, the bond in the LDC being effected by covalent bonding, electrostatic interactions, dipole moments, dispersion forces, ion interactions, hydrogen bridges and/or hydrophobic interactions.

30 Claims, No Drawings

LIPID MATRIX-DRUG CONJUGATES PARTICLE FOR CONTROLLED RELEASE OF ACTIVE INGREDIENT

A means for achieving a controlled drug administration is the use of particulate vehicles with a particle size in the micrometer range or in the nanometer range. The drug is incorporated into the vehicle, examples are O/W emulsions, liposomes, polymer microparticles, polymer nanoparticles, solid lipid nanoparticles, drug microparticles and drug nanoparticles (nanocrystals, nanosuspensions) (R. H. Müller, G. E. Hildebrand, Pharmazeutische Technologie: Moderne Arzneiformen, Wissenschaftliche Verlagsgesellschaft Stuttgart). The main purpose of using particulate vehicle systems is, in addition to the reduction of side effects, the establishment of an optimized drug release profile. As a rule, a sustained or at least a prolonged release is sought. High initial release (so-called burst release) is undesired. A standard example of this are polymer microparticles with LHRH analogues for the therapy of prostate carcinoma with a release period over four weeks (commercial products: Decapeptyl, Enantone).

A serious problem which in many cases cannot be solved is a high initial release occurring upon the incorporation of drugs into these drug vehicles. As a rule, emulsions are not suitable for a prolonged release as the active ingredient dissolved in the emulsion drops redistributes itself upon dilution (e.g. injection into the blood) within milliseconds into the aqueous blood phase (C. Washington, in (R. H. Müller, S. Benita, B. Böhm, Eds.) Emulsions and Nanosuspensions for the Formulation of Poorly Soluble Drugs, medpharm scientific publishers Stuttgart, 101–117, 1998). A prolonged release from liposomes is possible only to a limited extent as identical redistribution processes of the active ingredient and the metabolization of the phospholipids of the liposomes limit the release time. Only with a suitable preparation technique is a sufficiently prolonged release obtained with polymer microparticles (e.g. Decapeptyl), with an unsuitable preparation technique such as ASES (Aerosol Solvent Extraction System) (B. W. Müller et al., U.S. Pat. No. 5,043,280 (1991)), a very high initial release is obtained. The achievement of a prolonged release is even more difficult in the case of nanoparticles, as the diffusion paths are very short due to the smallness of the particles, and the degradation rate is sometimes very rapid. Drug release takes place instantly due to diffusion, something which was observed both with polymer nanoparticles and with solid lipid nanoparticles (zur Mühlen, A. et al. Eur. J. Pharm. Biopharm. 1998, 45, 149–155). In particular from poorly soluble drugs, microparticles can be prepared from pure active ingredient with size reduction processes. Due to the low water solubility of the active ingredients (in general associated with a low dissolution rate) in combination with the relatively low particle surface, a slow release process results. Examples are corticoid microparticle suspensions for intramuscular or intraarticular injection. For some application areas however, a longer release time would be desirable. By means of high-energy milling, poorly soluble drugs can be reduced to nanoparticles (nanocrystals, called nanosuspensions in aqueous dispersion) (Müller, R. H. et al., Pharm. Ind. 1999, 61, 1 74–78). Due to the greatly enlarged surface, however, dissolution is very rapid with nanocrystals. Intravenously injected nanosuspensions behaved pharmacokinetically like a solution (e.g. cyclosporine) (H. Sucker, in Pharmazeutische Technologie: Moderne Arzneiformen (R. H. Müller, G. E. Hildebrandt, Eds.), Wissenschaftliche Verlagsanstalt Stuttgart, 383–391, 1998).

However, microparticles with a size in the lower micrometer range and nanoparticles have advantages described in the literature for drug administration. Thus they adhere to the gastro-intestinal membrane after peroral application. As a result, the bioavailability increases, at the same time the variability decreases. Due to the particle fineness, poorly soluble drugs which do not display sufficient bioavailability after oral application can be injected intravenously (R. H. Müller, in Pharmazeutische Technologie: Moderne Arzneiformen (R. H. Müller, G. E. Hildebrand, Eds.) Wissenschaftliche Verlagsanstalt Stuttgart, 393–400, 1998). Thus a sufficiently high bioavailability is achieved even with poorly soluble drugs. Due to these advantages, it would be desirable to be able to prepare fine particles in which the fast release due to active ingredient diffusion is eliminated or at least minimized.

In the present invention, this is achieved by linking the drug to the matrix material of the particles by covalent bonds, electrostatic interactions, dipole moments, dispersion forces, ion interactions, hydrogen bonds and/or hydrophobic interactions.

Only one of these types of bond can be present, according to some versions according to the invention, or else several of these types of bond can also be present, according to other versions of the invention.

There are thus
a) Versions with covalent bonds,
b) Versions with non-covalent bonds and
c) Versions with a proportion of covalent and a proportion of non-covalent bonds In particular in the case of the versions with non-covalent bonds in the form of electrostatic interactions, dipole moments, dispersion forces, ion interactions, hydrogen bridges and/or hydrophobic interactions, a proportion of covalent bonding can also be present according to c) above.

Lipids are used as matrix material.

Conjugates from drugs or prodrugs with lipids are already described in the literature, the aim in this case being to increase membrane permeability and thus drug absorption by coupling an active ingredient with a lipophilic component. A prerequisite for a good absorption is however, in addition to membrane permeability, also a sufficiently high solubility in water. It is of no use if such a conjugate is very lipophilic but at the same time is not very water soluble. Due to the low water solubility, in this case, too little drug reaches the membrane. Dissolution rate and water solubility then become the rate-determining step of the absorption. To prevent this, the aim in the case of these lipid-prodrug conjugates was to prepare conjugates with as high a water solubility as possible. In the present invention, exactly the opposite is the case, the water solubility is to be as low as possible in order to minimize an initial release. The drug is to be released by degradation of the conjugate instead of by diffusion, i.e. after chemical cleavage of the conjugate (e.g. by enzymes in the gastro-intestinal tract or in other body fluids such as blood).

In the present invention, not only are stable conjugates produced by covalent bonds, but also the conjugates produced by non-covalent bonding are so stable, despite the absence of covalent bonding forces, that particles can be prepared from them.

Polymer-drug conjugates often have the problem that, as non-physiological components in the organism, they cannot, or can only slowly, be cleaved. Cleavage of the drug from the polymer is however a precondition for release and therapeutic effectiveness. To achieve a better degradation capability in vivo, lipids are therefore used as matrix material in the present invention. Toxicologically there is also the advantage that the lipid part can be metabolized after the cleavage of the conjugate. It serves at the same time as a nutrient.

In the case of lipid-prodrugs which still have corresponding water solubility, the degradation of the molecule takes place in solution. In the case of the insoluble particles described in this invention, it was found that the lipid conjugate, despite its solid aggregate state, can be degraded. This takes place by the anchoring of enzyme complexes on the particle surface, a surface degradation takes place in which the drug molecules are released (e.g. adsorption of the lipase/colipase complex in the gastro-intestinal tract). The better degradability of lipid-drug conjugates compared with polymer-drug conjugates can be explained in that e.g. the lipid-catabolizing enzymes in the organism are sometimes very unspecifically due to the chemical diversity of the lipids in food. Therefore, lipid-drug conjugates can also be processed accordingly. On the other hand, polymers such as e.g. polymethacrylates and polyhydroxybutyrates (PHBs) do not form part of the human diet. Although PHB is the energy-storage polymer of bacteria, it cannot be degraded by humans in vivo.

The particle matrix of the drug vehicles according to the invention is 100% composed of lipid-drug conjugate (LDC) (Example 1).

The preparation of LDC particles with covalent bonding is carried out e.g. by dispersion or precipitation, generally known methods described in pharmacy and process engineering textbooks being used. Upon dispersion, coarsly dispersed lipids are reduced by mechanical processes. The lipids can be in solid aggregate state (e.g. mortar mill) or in liquid aggregate state (e.g. emulsification of melted lipids by mixers). For the preparation of the LDC dispersion, the lipids can first be reduced and then dispersed in the external (e.g. aqueous) phase or alternatively reduced directly in the external phase. To produce superfine particles in the size range 1–10 $\mu$m and in particular in the nanometer range (<1000 nm), high pressure homogenization processes (piston-gap homogenizers, jet stream high pressure homogenizers such as e.g. Microfluidizer) and rotor-stator colloid mills are particularly suitable, the coarsly dispersed matrix material being dispersed in a liquid (e.g. water, non-aqueous media such as polyethylene glycol 400/600 and oils such as Miglyols). In liquid dispersion, the drug vehicles are physically stabilized by surfactants or polymers. No stabilizers are required in dispersion media with sufficiently high viscosity (surfactant-free dispersions). The drug vehicles according to the invention can also be present in a solid dispersion, i.e. the drug carriers are incorporated in a solid external phase, e.g. polyethylene glycol 10000.

Instead of consisting completely of lipid-drug conjugate (LDC), the matrix of the drug vehicles according to the invention can also have a lipid added to it, i.e. consist of a mixture of LDC with one or more lipids (i.e. the matrix is a blend). An example is the mixing of the LDC behenyl alcohol butyric acid ester with cetyl palmitate (example 2) or of the LDC tributyrin with compritol (triglyceride of behenic acid) (example 3). This is recommended in particular when a faster drug release is desirable and the degradation of the LDC is to be accelerated. The addition of a rapidly degradable lipid such as cetyl palmitate leads after its degradation to the enlargement of the surface and resultant rapid degradation of the LDC particles and subsequent drug release.

The preparation of a lipid conjugate with non-covalent bonds is carried out e.g. by melting of the conjugate-forming components (melting method) or by dissolving the components in a common solvent and then evaporating the solvent (dissolution method). Active ingredient and conjugate-forming lipid component are characterized in that that the molecules contain oppositely charged groups (e.g. quaternary ammonium group and dissociated carboxy group) or molecule parts which develop non-covalent interactions with each other (e.g. hydrophobic interactions). Examples of drugs with a primary amino or guanidine function are diminazene, trybizin hydrochloride (SISPI), pentamidine, melarsoprol, cisplatin and hydroxyurea.

Thus, e.g. in the melting method, active ingredient and oppositely charged second conjugate component (e.g. diminazene and stearic acid in the molar ratio 1:2, example 5) are mixed and heated, then cooled, and the conjugate has formed.

In the dissolution method, both components are dissolved in an aqueous or non-aqueous solvent (e.g. diminazene and stearic acid, molar ratio 1:2 in ethanol, example 6) and heated. After evaporation of the ethanol, the conjugate is obtained as residue. There can be used as solvents e.g. water, alcohols, oils, liquid polyethylene glycols (PEGs) or components liquefied by heating (e.g. PEGs or lipids such as Imwitor 900 solid at room temperature) and their mixtures.

A variety of different lipids can be used for the preparation of LDC dispersions. These are both chemically uniform lipids and their mixtures. The lipids are characterized in that they are present in the final product LDC dispersion in the crystalline state (e.g. $\beta$-, $\beta$i-modification) or in the liquid-crystalline state ($\alpha$-modification) or in a mixture thereof. When lipid mixtures are used, liquid lipids (e.g. oils, lipophilic hydrocarbons, lipophilic organic liquids such as oleic alcohol) can also be added to the solid lipids (e.g. glycerides, lipophilic hydrocarbons such as hard paraffin) (so-called "lipid blends").

For example, the following lipids are used as dispersed phase and can be applied as individual component or as mixture: Natural or synthetic triglycerides or mixtures of same, monoglycerides and diglycerides, alone or mixtures of same or with e.g. triglycerides, self-emulsifying modified lipids, natural and synthetic waxes, fatty alcohols, including their esters and ethers and in the form of lipid peptides, or any mixtures of same. Particularly suitable are synthetic monoglycerides, diglycerides and triglycerides as individual substances or as mixture (e.g. hard fat), Imwitor 900, triglycerides (e.g. glycerol trilaurate, glycerol myristate, glycerol palmitate, glycerol stearate and glycerol behenate) and waxes such as e.g. cetyl palmitate and white wax (DAB; German Pharmacopeia).

To stabilize the LDC dispersions or modify their surface in a controlled way, surfactants, stabilizers and polymers can be used which are generally known from the preparation of dispersions. Examples of these are:

1. sterically stabilizing substances such as poloxamers and poloxamines (polyoxyethylene-polyoxypropylene block copolymers), ethoxylated sorbitan fatty acid esters, in particular polysorbates (e.g. Polysorbate 80 or Tween 80®), ethoxylated mono- and diglycerides, ethoxylated lipids, ethoxylated fatty alcohols or fatty acids, and esters and ethers of sugars or of sugar alcohols with fatty acids or fatty alcohols (e.g. saccharose monostearate);
2. charged ionic stabilizers such as diacetyl phosphates, phosphatidylglycerol, lecithins of various origins (e.g. egg lecithin or soya lecithin), chemically modified lecithins (e.g. hydrogenated lecithins), as well as phospholipids and sphingolipids, mixture of lecithins with phospholipids, sterols (e.g. cholesterol and cholesterol derivatives as well as stigmasterol) and likewise saturated and unsaturated fatty acids, sodium cholate, sodium glycocholate, sodium taurocholate, sodium deoxycholate or their mixtures, amino acids or antiflocculants such as e.g. sodium citrate, sodium pyrophosphate, sodium sorbate [Lucks, J. S. et al. Int. J. Pharm., 1990, 58, 229–235]. Amphotheric surfactants such as e.g. (3-[(3-cholamidopropyl)-dimethylammonio]-2-hydroxy-1-propane sulphonates) [CHAPSO], (3-[(3-cholamidopropyl)-dimethylammonio]-1-propane sulphonates) [CHAPS] and N-dodecyl-N,N-dimethyl-3-ammonio-1propane sulphonate. Cationic surfactants, e.g. benzyldimethylhexadecylammonium chloride, methylbenzethonium chloride, benzalkonium chloride, cetylpyridinium chloride.

3. Viscosity increasing substances such as e.g. cellulose ethers and cellulose esters (e.g. methyl cellulose, hydroxyethyl cellulose, hydroxypropyl cellulose, sodium carboxy methyl cellulose), polyvinyl derivatives as well as polyvinyl alcohol, polyvinyl pyrrolidone, polyvinyl acetate, alginates, polyacrylates (e.g. carbopol), xanthanes and pectins.

The charged stabilizers are, if necessary or desired, preferably contained at the concentration of 0.01% to 20% (m/m) and in particular in a concentration of 0.05% to 10% in the LDC dispersion. Viscosity increasing substances are, if necessary or desired, incorporated in the formulation in a similar ratio, preferably in a quantity of 0.01–20% and in particular in a quantity of 0.1% to 10% (m/m) and preferably in the range between 0.5% and 5%.

There can be used as external phase (dispersion medium, continuous phase) water, aqueous solutions or liquids miscible with water, and glycerine or polyethylene glycol and oily liquids such as Miglyols (medium chain triglycerides—MCTs) and other oils (castor, peanut, soya, cottonseed, rape seed, linseed, olive, sunflower, saflor oil).

Surfactant-free LDCs are prepared by dispersion of the lipid phase in an aqueous solution which contains one or more viscosity increasing substances, either alone or in combination with other substances, as well as sugar, sugar alcohols, in particular glucose, mannose, trehalose, mannitol, sorbitol as well as others. Furthermore, it is possible to use a combination of the viscosity increasing substances or the combination of same with sugar or sugar alcohols or in a further combination with charge stabilizers or anti-flocculants.

The particle matrix can also consist of a mixture of one or more LDCs and one or more drugs. This can be used in particular when an initial dose is additionally required before a prolonged release.

The particle matrix of the drug vehicles according to the invention can also combine the above the principles, i.e. the matrix consists of a mixture of LDCs, one or more lipids and one or more drugs.

In the LDC particles, the drug can be coupled to various lipids, e.g. one or more diglycerides, monoglycerides, glycerol (e.g. tributyrin), fatty acids, fatty alcohols (e.g. behenyl alcohol-butyric acid ester), functional groups of sterols such as cholesterol and cholesterol derivatives and of waxes.

The bonding of drugs can take place covalently or non-covalently via other interactions (e.g. ion pairs) of various functional groups of the lipid, e.g. hydroxyl groups, carboxy, primary, secondary and quaternary amino groups. In addition to covalent bonding, there can optionally also be a proportion of non-covalent bonding, e.g. ion pairs (vitamin C with lecithin) or conversely, in addition to non-covalent bonding, there can optionally also be a proportion of covalent bonding.

According to the invention, there come into consideration in particular as drugs or drug groups:
  butyric acid and in particular behenyl alcohol-butyric acid ester and butyric acid triglyceride (tributyrin), and
  β-amino acids and peptides and proteins from these amino acids.

Examples of LDCs with covalent bonding are tributyrin, butyric acid derivatives (e.g. 4-(2-glyceryl)butyric acid, behenyl alcohol-butyric acid ester), retinol palmitate, tocopherol palmitate etc.

Tributyrin is a prodrug of butyric acid which effects cell differentiation in vitro in a large number of neoplastic cells. The clinical use of butyric acid is limited to date due to the difficulties in achieving effective therapeutic concentrations, due to its rapid metabolism [Z. X. Chen et al. Cancer Res. 54 (1994) 3494–3499]. One strategy to achieve effective butyric acid levels in vivo is to use butyric acid compounds as prodrugs which can be metabolized under in vivo conditions to give effective butyric acid concentrations. One of these compounds is tributyrin, 1,2,3 butyric acid glycerol ester, which displayed a high level of biological activity in in vitro trials [Z. X. Chen et al. Cancer Res. 54 (1994) 3494–3499, C. Schröder et al. Int. J. Oncol. 13 (1998) 335–1340]. Tributyrin was examined in a phase 1 study as an oral preparation in the treatment of solid tumors. The results were disappointing. No significant tumor regression had taken place. [B. A. Conley et al. Clin. Canc. Res. 4 (1998) 629–634]. This is a result of the rapid metabolism of tributyrin and butyric acid.

Solid lipid drug conjugates (LDCs) have been developed as a new concept of cancer treatment by means of tributyrin, or of the active compound butyric acid. On the one hand tributyrin in mixture with compritol, on the other an ester of behenyl alcohol and butyric acid. The formulation as solid particles opens up the possibility on the one hand of a retarded release of the active ingredient butyric acid, on the other the possibility of the concept of drug targeting, i.e. selective active ingredient application in defined areas. Thus it is possible e.g. to process the LDC particles in a drug formulation for colon delivery and thus to treat local colon carcinoma diseases. Furthermore it is possible to prepare the particles with specific surfactants which make possible a defined accumulation in specific body regions, e.g. Poloxamer 407, accumulation in the bone marrow in the case of leukemia diseases).

When preparing LDC particles by wet-milling of the particle matrix material in melted polyethylene glycol (PEG) 10.000 (e.g. at 80° C.), the external phase solidifies upon cooling to room temperature. A solid dispersion is produced, i.e. LDC particles embedded in solid PEG 10.000. This solid dispersion can be processed e.g. milled and processed as powder into tablets and pellets or packed in hard gelatine capsules. For packing in both soft and hard gelatine capsules, the solid dispersion can also be melted again and poured into the capsules in liquid state.

Preparation of dry products from LDC dispersions is possible with customary processing techniques such as e.g. spray-drying, lyophilization, roller drying and vacuum drying. The dry products can then be further processed to traditional drug forms such as e.g. tablets, capsules, pellets, sachets or dry products for reconstitution (e.g. for injectables).

EXAMPLES

Example 1

Preparation of drug vehicles from the lipid-drug conjugate (LDC) behenyl alcohol-butyric acid ester: The LDC was synthesized as follows: butyric acid chloride was reacted with behenyl alcohol in dichloromethane in the presence of the catalyst dimethylaminopyridine (DMPA) at room temperature and purified by recrystallization from acetone. For preparation of the LDC particles, the LDC was melted at 46° C. and dispersed in an aqueous surfactant solution with a rotor-stator mixer (Ultra-Turax, Jahnke und Kunkel, Germany, 10,000 rpm, for 1 minute). The surfactant solution consisted of 5% poloxamer 188 in water. The raw emulsion obtained was then homogenized in a high pressure homogenizer Micron LAB 40 at 500 bar applying 3 cycles. The particle size was measured by photon correlation spectroscopy (PCS) and laser diffractometry (LD, volume distribution). The PCS diameter was 149 nm, the polydispersion index was 0.196. The 90% LD diameter—a measurement of the proportion of micrometer particles—was 0.39 µm, i.e. the contamination by micrometer particles was extremely low.

Example 2

Preparation of drug vehicles from the LDC behenyl alcohol-butyric acid ester in lipid mixture: The LDC was synthesized as in Example 1. 1 part LDC was then mixed with 1 part cetyl palmitate, melted and then processed as in Example 1. The PCS diameter was 203 nm, the polydispersion index 0.210.

Example 3

Preparation of drug vehicles from tributyrin-lipid mixture: Tributyrin was mixed with the lipid compritol in the ratio 3 parts to 7 parts and then processed analogously to Example 1 to a lipid particle dispersion. The average PCS diameter was 268 nm, the polydispersion index 0.248.

Example 4

The effectiveness of tributyrin drug vehicles was measured in HL 60 tumor cells (human myeloid leukemia cell line). HL 60 cells are a sensitive indicator of the effect of tributyrin. It brings about a differentiation of the tumor cells to granulocyte-like cells. The latter have the property of reducing NBT (nitro-blue tetrazolium) to a blue dye (H. P. Koeffler et al. Blood 62 1 (983) 709–721). Tributyrin-compritol particles, consisting of equal parts of tributyrin and compritol (glycerine tribehenate) were prepared as in Example 1. The overall lipid concentration was 5%, the Poloxamer 188 concentration likewise 5%. The particle size was 147 nm (PCS diameter), the polydispersion index 0.321. The differentiation effect was compared with that of free tributyrin, dissolved in ethanol. The effective 50% dosage (ED 50%) of free tributyrin was 130 µM. An adequate quantity of tributyrin-compritol nanoparticle dispersion was, like the corresponding quantities of surfactant solution and pure compritol particle dispersion, added to HL 60 cells and the NBT reduction ascertained after 6 days' incubation time at 37° C. and 5% carbon dioxide content. FIG. 1 shows that the differentiating effect corresponded to 80% of the effect of free tributyrin.

Example 5

Preparation of a diminazene-stearic acid conjugate via the melt method:

Diminazene and stearic acid were mixed in the molar ratio 1:2 and heated. A yellow conjugate resulted.

Example 6

Preparation of a diminazene-stearic acid conjugate via the dissolution method: Diminazene and stearic acid were dissolved in ethanol in the molar ratio 1:2 and heated. After complete dissolution of both components, the ethanol was evaporated and a yellow conjugate obtained as residue (identical to Example 5).

Example 7

Preparation of LDC nanoparticles via cold homogenization: The diminazene stearic acid conjugate from Example 5 was dispersed in a surfactant solution (1% Tween 80) and homogenized in the solid state at room temperature with a high pressure homogenizer (Micron LAB 40, APV Deutschland GmbH, Lübeck, Germany) at 15,000 bar with 15 cycles. After 15 cycles, a dispersion of diminazene stearic acid nanoparticles is obtained. The average diameter measured by photon correlation spectroscopy (PCS, Malvern Zetasizer 4, Malvern Instruments, UK) was 314 nm (standard deviation: 14 nm) with a polydispersion index (PI) of 0.214 (standard deviation 0.01). The 95% diameter measured by laser diffractometry was 0.693 µm (Coulter LS 230, Coulter Electronics, Germany).

Example 8

Preparation of LDC nanoparticles by the dissolution method: The diminazene-stearic acid conjugate was dissolved in 96% ethanol (2.5% m/m) and pumped with a perfusor (Braun Melsungen, Germany) at a rate of 60 ml/h into 40 ml of a 1% Tween 80 solution. The cannula system used was Venofix S, 30 cm, 0.5 mm–25G. An ultrasound rod was dipped into the solution. The time of the inflow was 20 minutes. The particle size was measured by PCS and laser diffractometry (LD): PCS diameter 462 nm with a PI value of 0.255. The 95% LD diameter was 0.488 µm.

If desired, the ethanol can be removed by evaporation. After evaporation of the ethanol in the rotary evaporator, the PCS diameter was 456 nm and the PI value 0.275, i.e. particle size and distribution remained unchanged.

Example 9

Analogously to example 5, diminazene was reacted with oleic acid, a liquid fatty acid.

Example 10

The diminazene-oleic acid conjugate from Example 9 was high pressure homogenized analogue to example 7. The conjugate nanoparticles obtained had a PCS diameter of 472 nm and a PI of 0.268. The 95% LD diameter was 0.707 µm.

Example 11

Analogously to example 5, SISPI was used as drug and processed to nanoparticles as in example 7 by high-pressure homogenization. The PCS diameter was 421 nm, the polydispersion index 0.207.

What is claimed is:

1. Particulate active ingredient vehicles (carriers) which are in the solid aggregate state at room temperature (20° C.), consisting essentially of a pure lipid-drug conjugate (LDC) or a mixture of several LDC's as particle matrix, the bond between the lipid and the drug in the LDC being covalent bonding, electrostatic interactions, dipole-dipole interactions, dispersion forces, ion interactions, hydrogen bonds and/or hydrophobic interactions in nature.

2. Particulate active ingredient vehicles according to claim 1 in which a proportion of covalent bonding is present.

3. Particulate active ingredient vehicles according to claim 1 with an average particle size in the range from 10–1000 nanometers.

4. Particulate active ingredient vehicles according to claim 1 with an average particle size in the range from 1–1000 micrometers.

5. Particulate active ingredient vehicles according to claim 1 in which one or more lipids are added to the LDC matrix.

6. Particulate active ingredient vehicles according to claim 5 in which 0.1% to 50% added lipid, relative to the overall weight, is contained in the particle matrix.

7. Particulate active ingredient vehicles according to claim 5 in which 50% to 99.9% added lipid, relative to the overall weight, is contained in the particle matrix.

8. Particulate active ingredient vehicles according to claim 1 in which one or more drugs are added to the LDC matrix.

9. Particulate active ingredient vehicles according to claim 8 in which the added drug is identical to the drug coupled to the lipid in the LDC.

10. Particulate active ingredient vehicles according to claim 1 in which the LDC was prepared by coupling a drug to one or more diglycerides, monoglycerides, glycerine, fatty acids, fatty alcohols, functional groups of lipids and waxes, alone or in mixture.

11. Particulate active ingredient vehicles according to claim 1 in which the LDC contains butyric acid as drug.

12. Particulate active ingredient vehicles according to claim 1 in which the LDC contains as drug β-amino acid, a peptide or a protein of this amino acid.

13. Particulate active ingredient vehicles according claim 1 which are prepared by reducing the material of the particle matrix with powder mills.

14. Particulate active ingredient vehicles according to claim 1 which were prepared by reducing the material of the particle matrix after suspension in an aqueous or non-aqueous liquid (wet-milling).

15. Particulate active ingredient vehicles according to 14 which were prepared by reducing the material of the particle matrix in a melted or partly melted state after suspension in an aqueous or non-aqueous liquid (wet milling).

16. Particulate active ingredient vehicles according to 1 which were prepared by reducing the material of the particle matrix in a melted or partly melted state by distribution in a gas phase or by distribution in a liquid phase.

17. Particulate active ingredient vehicles according to claim 1 which are present in the form of a liquid dispersion, solid dispersion or a dry form by removal of liquid from the liquid dispersion.

18. Particulate active ingredient vehicles according to claim 10 in which the LDC was prepared by coupling a drug to one or more sterols.

19. Particulate active ingredient vehicles according to claim 10 in which the LDC was prepared by coupling a drug to cholesterol, cholesterol derivatives and/or stigmasterol, alone or in mixture.

20. Particulate active ingredient vehicles according to claim 11 in which the LDC contains behenyl alcohol butyric acid ester or butyric acid triglyceride (tributyrin) as the drug.

21. Particulate active ingredient vehicles according to claim 14 which are prepared by reducing the material of the particle matrix by milling with a mortar mill, ball mill, cross-beater mill or gas jet mill.

22. Particulate active ingredient vehicles according to claim 14 which were prepared by reducing the material of the particle matrix after suspension in a colloid-stator mill, a piston-gap high pressure homogenizer, a flow-dispersing machine of the jet stream type or by a static mixer in microscale and in macroscale.

23. Particulate active ingredient vehicles according to claim 14 which were prepared by reducing the material of the particle matrix after suspension in an Ultra-Turrax or a Silverson homogenizer, a Microfluidizer or a Sulzer mixer.

24. Particulate active ingredient vehicles according to claims 16 which were prepared by reducing the material of the particle matrix in the melted or partly melted state by distribution in a gas phase.

25. Particulate active ingredient vehicles according to claims 16 which were prepared by reducing the material of the particle matrix in the melted or partly melted state by distribution a liquid phase by atomization by means of single-substance nozzles in water.

26. Particulate active ingredient vehicles according to claim 17 which are present in the form of a liquid dispersion, solid dispersion or a dry form by removal of liquid from the liquid dispersion using spray-drying, lyophilization, and roller drying.

27. Particulate active ingredient vehicles according to claim 1, wherein the drug and lipid are oppositely charged.

28. Particulate active ingredient vehicles according to claim 1, further comprising a charged stabilizer.

29. Particulate active ingredient vehicles according to claim 1, further comprising a surfactant.

30. Particulate active ingredient vehicles (carriers) which are in the solid aggregate state at room temperature (20° C.), consisting essentially of a pure lipid-drug conjugate (LDC) or a mixture of several LDC's as particle matrix, the bond between the lipid and the drug in the LDC comprising electrostatic interactions.

\* \* \* \* \*